(12) United States Patent
Zavesky et al.

(10) Patent No.: US 10,783,727 B2
(45) Date of Patent: Sep. 22, 2020

(54) NETWORK CONTROLLED PHYSICAL ACCESS RESTRICTION BASED UPON PHYSIOLOGICAL STATE

(71) Applicant: AT&T Intellectual Property I, L.P., Atlanta, GA (US)

(72) Inventors: Eric Zavesky, Austin, TX (US); Gregory Edwards, Austin, TX (US)

(73) Assignee: AT&T Intellectual Property I, L.P., Atlanta, GA (US)

(*) Notice: Subject to any disclaimer, the term of this patent is extended or adjusted under 35 U.S.C. 154(b) by 0 days.

(21) Appl. No.: 16/741,378

(22) Filed: Jan. 13, 2020

(65) Prior Publication Data

US 2020/0151985 A1    May 14, 2020

Related U.S. Application Data

(63) Continuation of application No. 16/378,267, filed on Apr. 8, 2019, now Pat. No. 10,535,208, which is a
(Continued)

(51) Int. Cl.
*G07C 9/25* (2020.01)
*G01N 33/487* (2006.01)
(Continued)

(52) U.S. Cl.
CPC ............ *G07C 9/253* (2020.01); *A61B 5/0022* (2013.01); *A61B 5/0205* (2013.01); *A61B 5/082* (2013.01); *A61B 5/1113* (2013.01); *A61B 5/4833* (2013.01); *B64C 39/02* (2013.01); *G01N 33/487* (2013.01); *G01N 33/497* (2013.01); *G06K 9/00892* (2013.01); *G07C 9/00563* (2013.01); *G07C 9/00571* (2013.01); *G07C 9/00896* (2013.01); *A61B 3/112* (2013.01);
(Continued)

(58) Field of Classification Search
None
See application file for complete search history.

(56) References Cited

U.S. PATENT DOCUMENTS 8,763,070 B2    6/2014  Cozart et al.
9,300,925 B1    3/2016  Zhang
(Continued)

OTHER PUBLICATIONS

Jutel, Dominique; Machine Translation of Publication No. FR 3040521 A1, Published on Mar. 3, 2017, Application No. FR 20150057945 A, Filed on Aug. 26, 2015; IP.com.

*Primary Examiner* — Carlos Garcia (57) ABSTRACT

Methods, computer-readable media, and devices are disclosed for providing an access restriction of a second person to a location associated with a first person in a managed environment in connection with a physiological state of the second person. For example, a method may include a processing system having a processor receiving a security plan for a first person that pertains to a second person. The security plan may define an access restriction of the second person to a location associated with the first person in a managed environment in connection with a physiological state of the second person. The processing system may further detect the second person in the managed environment, detect the physiological state of the second person, and control an automated barrier in the managed environment in accordance with the security plan to provide the access restriction when the physiological state of the second person is detected.

20 Claims, 3 Drawing Sheets

Related U.S. Application Data continuation of application No. 15/682,067, filed on Aug. 21, 2017, now Pat. No. 10,255,733.

(51) Int. Cl.

| | | |
|---|---|---|
| *G01N 33/497* | (2006.01) | |
| *A61B 5/00* | (2006.01) | |
| *A61B 5/08* | (2006.01) | |
| *B64C 39/02* | (2006.01) | |
| *G07C 9/00* | (2020.01) | |
| *A61B 5/11* | (2006.01) | |
| *A61B 5/0205* | (2006.01) | |
| *G06K 9/00* | (2006.01) | |
| *A61B 5/117* | (2016.01) | |
| *A61B 5/16* | (2006.01) | |
| *A61B 3/11* | (2006.01) | |

(52) U.S. Cl.
CPC ............ *A61B 5/117* (2013.01); *A61B 5/165* (2013.01); *A61B 5/4845* (2013.01); *A61B 5/6898* (2013.01); *A61B 2560/0242* (2013.01); *B64C 2201/127* (2013.01); *G06K 2009/00939* (2013.01)

(56) References Cited

U.S. PATENT DOCUMENTS

| | | |
|---|---|---|
| 9,329,758 B2 | 5/2016 | Guzak et al. |
| 9,348,985 B2 | 5/2016 | Davis et al. |
| 9,400,879 B2 | 7/2016 | Tredoux et al. |
| 9,531,708 B2 | 12/2016 | Cornell et al. |
| 9,531,710 B2 | 12/2016 | Deutschmann et al. |
| 9,654,977 B2 | 5/2017 | Aissi |
| 9,667,366 B2 | 5/2017 | Herickhoff et al. |
| 2008/0104415 A1 | 5/2008 | Palti-Wasserman et al. |
| 2010/0295656 A1 | 11/2010 | Herickhoff et al. |
| 2011/0254681 A1 | 10/2011 | Perkinson et al. |
| 2015/0061825 A1 | 3/2015 | Suzuki et al. |
| 2015/0089240 A1 | 3/2015 | Itkis |
| 2015/0167995 A1 | 6/2015 | Fadell et al. |
| 2015/0265201 A1 | 9/2015 | Arbas |
| 2016/0239649 A1 | 8/2016 | Zhao |
| 2016/0266577 A1 | 9/2016 | Kerzner |
| 2016/0284142 A1 | 9/2016 | Elbling et al. |
| 2017/0092109 A1 | 3/2017 | Trundle et al. |
| 2017/0094049 A1 | 3/2017 | Kanevsky et al. |
| 2017/0134171 A1 | 5/2017 | Woxland et al. |
| 2018/0225780 A1 | 8/2018 | Boss et al. |

NETWORK CONTROLLED PHYSICAL ACCESS RESTRICTION BASED UPON PHYSIOLOGICAL STATE

This application is a continuation of U.S. patent application Ser. No. 16/378,267, filed Apr. 8, 2019, now U.S. Pat. No. 10,535,208, which is a continuation of U.S. patent application Ser. No. 15/682,067, filed Aug. 21, 2017, now U.S. Pat. No. 10,255,733, all of which are herein incorporated by reference in their entirety.

The present disclosure relates generally to smart buildings, smart homes, and the like, and more particularly to devices, computer-readable media, and methods for providing an access restriction of a second person to a location associated with a first person in a managed environment in connection with a physiological state of the second person.

BACKGROUND

Current trends in wireless technology are leading towards a future where virtually any object can be network enabled and Internet Protocol (IP) addressable. The pervasive presence of wireless networks, including cellular, Wi-Fi, Zig-Bee, satellite and Bluetooth networks, and the migration to a 128-bit IPv6-based address space provides the tools and resources for the paradigm of the Internet of Things (IoT) to become a reality.

SUMMARY

In one example, the present disclosure discloses a method, computer-readable medium, and device for providing an access restriction of a second person to a location associated with a first person in a managed environment in connection with a physiological state of the second person. For example, a method may include a processing system having a processor receiving a security plan for a first person that pertains to a second person. The security plan may define an access restriction of the second person to a location associated with the first person in a managed environment in connection with a physiological state of the second person. The processing system may further detect the second person in the managed environment, detect the physiological state of the second person, and control an automated barrier in the managed environment in accordance with the security plan to provide the access restriction when the physiological state of the second person is detected.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses methods, computer-readable media, and devices for providing an access restriction of a second person to a location associated with a first person in a managed environment in connection with a physiological state of the second person. In particular, examples of the present disclosure automatically restrict access for a specific individual to a location associated with another person through digital and physical mechanisms. Examples of the present disclosure may also provide for different levels of access based on the comfort level of the other person or legal mandate. The location associated with the other person may comprise the current location of the other person, or a location in which the other person has a right of possession or visitation, or which is otherwise frequented by the other person. In particular, examples of the present disclosure are intended for deployment in closed/managed environments, e.g., private premises, such as gated communities, apartment and office buildings, corporate or educational campuses, and the like. As such, examples of the present disclosure provide advancements in premises security technologies. For instance, a network of devices, including a controller allows the simultaneous monitoring of multiple locations throughout a managed environment and provides for precise identification of individuals for which automated physical restrictions are to be applied.

Physical identification of an individual subject to an access restriction in accordance with a security plan may be accomplished through different biometric factors such as facial recognition, voice recognition, gait detection, fingerprint scanning, and the like, using sensors throughout the managed environment. In one example, detection of an individual may also include detection of any mobile device that is associated with the individual, e.g., through Global Positioning System (GPS) location information, near-field communication (NFC) sensing, and so forth. Alternatively, or in addition, a vehicle of the individual may be detected through license plate scanning, or through wireless communication with an on-board computing system of the individual's vehicle, for instance. In one example, an individual's whereabouts in a managed environment may be tracked and physical access to another person may be prevented through any security devices, e.g., such as powered locks, doors, windows, gates, elevators, garage doors, and the like that are remotely controllable. In one example, any machine that has remote access, such as a car, a computer, a phone, etc. and that belongs to the other person could also be disengaged with regard to being accessed by the individual, or access to such items for the individual through the security devices may also be prevented.

In one example, different levels of access for an individual to another person may be implemented. For instance, the individual may be given partial access to the other person based on a combination of parameters related to physiological state(s), time, and/or location. It should be noted that as referred to herein, a physiological state may comprise, for example, a physical/biometric state, such as having an elevated heart rate, having dilated pupils, having a high breathing rate, having an elevated sweat level, engaging in erratic walking, clenching fists, carrying a weapon or an object that can be used as a weapon, having slurred speech or incoherent speech, having a high level of detectable alcohol fume, and so forth. In addition, as referred to herein a physiological state may comprise an emotional state. For instance, an emotional state may be determined from several measurable or observable physical/biometric characteristics. An emotional state may also be determined from outgoing electronic communications or speech of an individual such as by matching particular keywords and phrases indicative of emotion.

In one example, the individual may opt-in to allowing physiological (biometric and/or emotional) monitoring to provide automated access restrictions and warnings to the other person. For instance, the individual may be a family member with an illness that is controllable with medication, and may voluntarily agree to physiological (biometric and/or emotional) monitoring, in order to have full and/or partial access to a location, or locations associated with the other person, e.g., another family member such as a spouse or a child. Thus, the level of access or restraint applied to the individual may be based on his or her emotion, soberness, or the like to avoid unwanted situationally dependent conflict or disturbance. In one example, determination of an emotional state of the individual may be based upon the individual's digital communications, such as social media posts, emails, text messages, and so forth, as well as automated assessment of the individual, e.g., based upon gait, speech, facial demeanor, and the like, from devices within the control of the system. For instance, a security camera at the entrance to a gated community may capture images and/or video of the individual, from which the system may make an automated determination of the physiological and/or emotional state of the individual, for the purpose of determining whether to allow or deny access to the other person through a security gate.

In one example, devices of the individual may also be used to determine the individual's physiological state. For example, a fingerprint scan via a fingerprint scanner in the managed environment and/or on a mobile device of the individual may be used to detect drug use. In the latter example, an application on the mobile device may be used to capture the fingerprint scan, transmit the captured fingerprint scan to a network-based device for analysis, and a notification may be provided to the system from the network-based device to allow the system to decide whether to allow or deny access to the individual. In one example, the individual may carry a spectrometer, such as a miniature mass spectrometer, e.g., using surface enhanced Raman spectroscopy (SERS), or the like. Accordingly, when the individual is detected in a managed environment, the individual may be prompted to self-test using the spectrometer. For example, the spectrometer may analyze the breath sample and provide results to a network-based device via a wireless connection. Alternatively, or in addition, the individual may be prompted to present the display results to a security camera, which may capture an image of a screen showing the results, and may compare the results to a set of criteria to determine whether the results are positive or negative for the detection of a controlled substance.

In one example, audio speakers throughout the environment may be used to provide instructions and warnings to the individual. For instance, if access by the individual is denied, a message may be presented to the individual via one or more speakers to leave the premises. Similarly, cameras in the managed environment may continue to record the movements and actions of the individual, e.g., until he or she voluntarily leaves, until security personnel or law enforcement arrives, until the other person actively disengages the access restrictions, e.g., via user inputs via the security plan, etc. These and other aspects of the present disclosure are discussed in greater detail below in connection with the examples of FIGS. 1-3.

Figure 1:
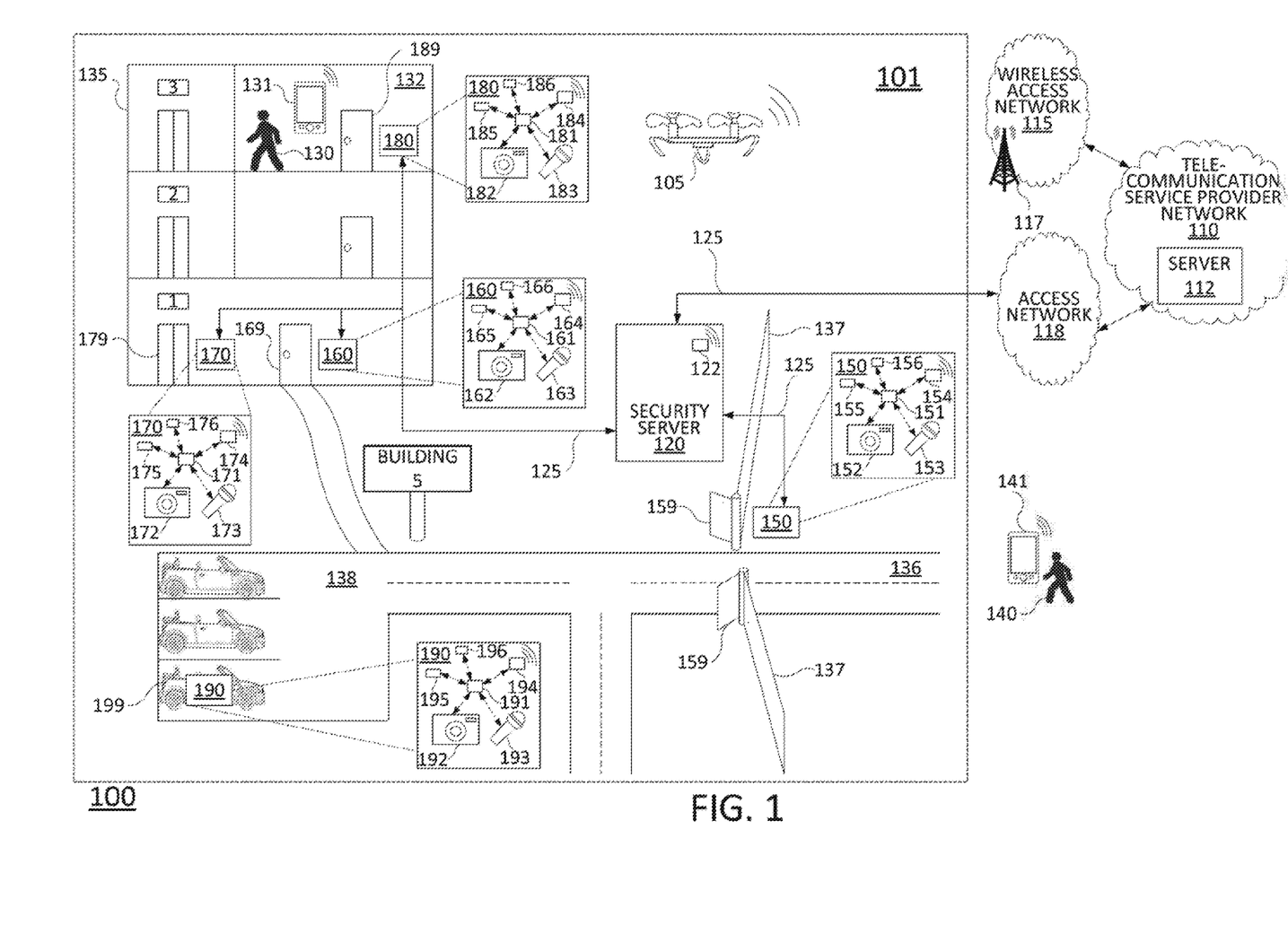
FIG. 1 illustrates an example system related to the present disclosure.

To aid in understanding the present disclosure, FIG. 1 illustrates a block diagram depicting one example of a system 100 suitable for performing or enabling the steps, functions, operations, and/or features described herein. The overall communications system 100 may include any number of interconnected networks which may use the same or different communication technologies.

In one example, the system 100 includes a telecommunication service provider network 110. In one example, telecommunication service provider network 110 may comprise a core network, a backbone network or transport network, such as an Internet Protocol (IP)/multi-protocol label switching (MPLS) network, where label switched routes (LSRs) can be assigned for routing Transmission Control Protocol (TCP)/IP packets, User Datagram Protocol (UDP)/IP packets, and other types of protocol data units (PDUs), and so forth. It should be noted that an IP network is broadly defined as a network that uses Internet Protocol to exchange data packets. However, it will be appreciated that the present disclosure is equally applicable to other types of data units and transport protocols, such as Frame Relay, and Asynchronous Transfer Mode (ATM). In one example, the telecommunication service provider network 110 uses a network function virtualization infrastructure (NFVI), e.g., host devices or servers that are available as host devices to host virtual machines comprising virtual network functions (VNFs). In other words, at least a portion of the telecommunication service provider network 110 may incorporate software-defined network (SDN) components.

The telecommunication service provider network 110 may be in communication with one or more access networks. For instance, wireless access network 115 may comprise a cellular network (e.g., a Universal Mobile Telecommunications System (UMTS) terrestrial radio access network (UTRAN), an evolved UTRAN (eUTRAN), a base station subsystem (BSS), e.g., a Global System for Mobile communication (GSM) radio access network (GRAN), a 2G, 3G, and/or 4G network, a Long Term Evolution (LTE) network, and the like). In such examples, telecommunication service provider network 110 may include evolved packet core (EPC) network components, network switching subsystem (NSS)/GSM core network and/or General Packet Radio Service (GPRS) core network components, and so forth. In another example, wireless access network 115 may comprise an Institute for Electrical and Electronics Engineers (IEEE) 802.11/Wi-Fi network, an IEEE 802.16 network, e.g., a wireless wide area network (WWAN) or WiMAX network, or the like. Thus, in one example, wireless access network 115 may include at least one wireless transceiver 117, which may alternatively comprise a cellular base station, such as a base transceiver station (BTS), a NodeB, an evolved NodeB (eNodeB), and the like, a non-cellular wireless access point, and so forth. In one example, access network 118 may comprise a wired access network such as a circuit switched access network, a cable network, a digital subscriber line (DSL) network, a metropolitan area network (MAN), an Internet service provider (ISP) network, and the like, and so forth. The telecommunication service provider network 110 and the access networks 115 and 118 may be operated by different service providers, the same service provider, or a combination thereof.

As illustrated in FIG. 1, system 100 also includes a managed environment 101. For example, managed environment 101 may comprise a local area network (LAN), a wireless LAN (WLAN), a Bluetooth network, a ZigBee network, and so forth, or a combination of interconnected devices using a plurality of such communication modalities and protocols. For instance, managed environment 101 may be a home network, an office network, a campus network, a network of a private residential community or an apartment building, a network of a recreational complex, and so forth. As illustrated, managed environment 101 may include a number of security units 150, 160, 170, 180, and 190. Each of the security units may include a processing unit (e.g., 151, 161, 171, 181, and 191), which may comprise a computing system, such as computing system 300 depicted in FIG. 3, specifically configured to perform various steps, functions, and/or operations in connection with examples of the present disclosure for providing an access restriction of a second person to a location associated with a first person in a managed environment in connection with a physiological state of the second person.

Each of the security units 150, 160, 170, 180, and 190 may also include, coupled to the respective processing unit 151, 161, 171, 181, or 191, a camera (e.g., 152, 162, 172, 182, and 192), a microphone (e.g., 153, 163, 173, 183, and 193), a speaker (e.g., 155, 165, 175, 185, and 195), and a fingerprint scanner (e.g., 156, 166, 176, 186, and 196). As illustrated in FIG. 1, each of the security units 150, 160, 170, 180, and 190 also includes a respective wireless transceiver (e.g., 154, 164, 174, 184, and 194), which may comprise an IEEE 802.11/Wi-Fi transceiver (e.g., a wireless router), an IEEE 802.15 based transceiver (e.g., a Bluetooth beacon or a ZigBee access point), an IEEE 802.16 (e.g., wireless metropolitan area network/WiMAX) transceiver, a cellular transceiver, and so forth. In one example, the security units 150, 160, 170, 180, and 190 may be in communication with a security server 120 via the respective wireless transceivers 154, 164, 174, 184, and 194 and wireless transceiver 122 of the security server 120. As further illustrated in FIG. 1, the security units 150, 160, 170, 180, and 190 may also be in communication with security server 120 via wired connections 125. In one example, the security units 150, 160, 170, 180, and 190 may also communicate with any wireless devices within a communication range of the respective wireless transceivers 154, 164, 174, 184, and 194, such as mobile device 131 of person 130 and mobile device 141 of individual 140. Mobile devices 131 and 141 may comprise, for example, any type of wireless communication-capable mobile telephony and computing device (broadly, a "mobile device"), such as: a mobile phone, a smartphone, a computing tablet, a messaging device, a personal computer, a laptop computer, a Personal Digital Assistant (PDA), and the like. For instance, mobile devices 131 and 141 may be equipped with at least one cellular radio/transceiver for cellular communications. Mobile devices 131 and 141 may also be equipped for any number of different modes of communication. For instance, mobile devices 131 and 141 may alternatively or additionally be equipped with an IEEE 802.11 (Wi-Fi) transceiver, an IEEE 802.16 (e.g., wireless metropolitan area network/WiMAX) transceiver, an IEEE 802.15 transceiver (e.g., Bluetooth, ZigBee, etc.), and so on. Alternatively, or in addition, the security units 150, 160, 170, 180, and 190 may be in communication with a server 112 in telecommunication service provider network 110 via the wireless transceivers 154, 164, 174, 184, and 194, wireless transceiver 117, and wireless access network 115.

In the example of FIG. 1, the security units 150, 160, 170, 180, and 190 are illustrated as having the same or substantially similar configurations and components. However, it should be understood that in other, further, and different examples, a security unit may include more or less components, or may have a different configuration. For instance, a security unit may omit a microphone, a fingerprint scanner, and so forth, or may include a barcode scanner, a near field communication (NFC) reader, an infrared sensor, or the like, which may be capable of reading a keycard, key fob, or other hardware tokens that may be carried by an individual.

As further illustrated in FIG. 1, the security units 150, 160, 170, 180, and 190 are paired with respective automated barriers, such as gate 159, door 169, elevator 179, door 189, and vehicle 199. In accordance with the present disclosure, gate 159, door 169, elevator 179, door 189, and vehicle 199 may be remotely controlled (locked and unlocked, closed and opened, etc.), via the respective processing unit 151, 161, 171, 181, and 191 of security units 150, 160, 170, 180, and 190. It should be noted that for ease of illustration, the actual locking mechanisms and the connections between the security units 150, 160, 170, 180, and 190 and the respective automated barriers are omitted from FIG. 1.

Figure 3:
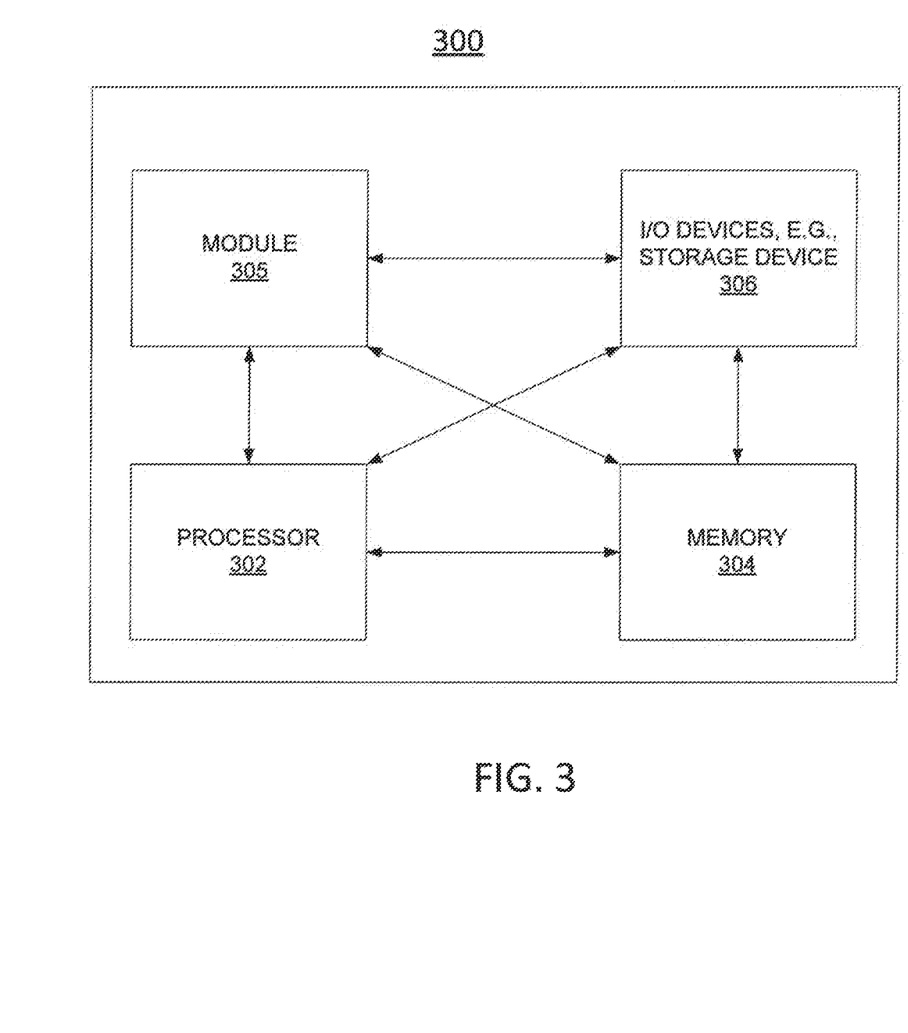
FIG. 3 illustrates an example high-level block diagram of a computer specifically programmed to perform the steps, functions, blocks, and/or operations described herein.

The various components of managed environment 101 described above may be utilized in connection with various examples of providing an access restriction of a second person to a location associated with a first person in a managed environment in connection with a physiological state of the second person. For instance, in one example, security server 120 may comprise a computing system, such as computing system 300 depicted in FIG. 3, specifically configured to perform various steps, functions, and/or operations in connection with examples of the present disclosure for restricting access of a second person to a location associated with a first person in a managed environment in connection with a physiological state of the second person, such as: receiving a security plan for a first person that pertains to a second person, detecting the second person in the managed environment, determining that the second person is within a predefined proximity of the location associated with the first person in accordance with the security plan, detecting a physiological state of the second person, controlling an automated barrier in the managed environment in accordance with the security plan to provide an access restriction when the physiological state of the second person is detected, and so on. It should be noted that the terms "configure" and "reconfigure" may refer to programming or loading a processing system with computer-readable/computer-executable instructions, code, and/or programs, e.g., in a distributed or non-distributed memory, which when executed by a processor, or processors, of the processing system within a same device or within distributed devices, may cause the processing system to perform various functions. Such terms may also encompass providing variables, data values, tables, objects, or other data structures or the like which may cause a processing system executing computer-readable instructions, code, and/or programs to function differently depending upon the values of the variables or other data structures that are provided. As referred to herein a "processing system" may comprise a computing device including one or more processors, or cores (e.g., as illustrated in FIG. 3 and discussed below) or multiple computing devices collectively configured to perform various steps, functions, and/or operations in accordance with the present disclosure.

To illustrate, individual 140 may comprise a family member with an illness that is controllable with medication, and may voluntarily agree to physiological (e.g., biometric and/or emotional) monitoring, in order to have full and/or partial access to a location, or locations associated with a person 130 physically residing within or traversing through the managed environment 101. For instance, managed environment 101 may comprise a residential complex where the person 130 lives on the third floor of an apartment building 135 (illustrated as "Building 5" in FIG. 1). The residential complex may include an access road 136 that passes through an entry gate 159. In one example, security server 120 may store a security plan for the person 130 pertaining to an individual 140. The security plan may be provided to the security server 120 from the mobile device 131, or from another device of the person 130, such as a personal computer. In one example, the security plan may be provided to the security server from a device of a security personnel of the managed environment 101. For instance, the security personnel may set up the security plan for the person 130 after confirming e.g., a court order, instructions from a physician or psychiatrist, or the like regarding the access of individual 140 to the person 130.

The security plan may provide for the individual 140 to be allowed or denied access to the person 130 based on one or more parameters related to the physiological state(s), e.g., emotion, soberness, etc., time, and/or location. For example, the security plan may allow individual 140 to access person 130 during daytime hours within the managed environment 101 when the individual 140 is (or is not in a particular physiological state), allow individual 140 to access person 130 during evening hours only within open or public areas of the managed environment 101 when the individual 140 is (or is not in a particular physiological state), and to otherwise deny access if such parameters are not met. In one example, the security plan may also include one or more types of identification data relating to the individual 140, such as, a reference photograph or a reference Eigen-face of the individual 140, a reference video of a gait of the individual 140, a reference audio of a voice of the individual 140, a telephone number, a Media Access Control (MAC) address or other identifiers of one or more mobile devices 141 belonging to the individual 140, and so on.

Continuing with the present example, individual 140 may be approaching the entry gate 159 of the managed environment 101 on foot via the access road 136. Security server 120 may first detect the presence of individual 140 at or within the managed environment 101 via security unit 150. For example, wireless transceiver 154 of security unit 150 may be within communication range of and receive a communication from mobile device 141. The communication may include an identifier of the mobile device 141 which processing unit 151 may match to a stored identifier for mobile device 141 and which is also associated with the individual 140. Similarly, an image or video of individual 140 may be captured via camera 152 as the individual 140 approaches the entry gate 159. The security server 120 may then compare the image and/or video to the stored identification data associated with a plurality of individuals including individual 140 to determine if there is a match. A similar process may involve collecting an audio recording of a voice of individual 140 via microphone 153 and comparing the recording to the stored audio recordings of a plurality of individuals including individual 140 to determine if there is a voice match.

In one example, the individual 140 may be detected at or within the managed environment 101, or at a particular location at or within the managed environment 101 using location information regarding the mobile device 141 from telecommunication service provider network 110. For example, server 112 in telecommunication service provider network 110 may track GPS location information of mobile device 141, and/or may track the general location of mobile device 141 via base station triangulation and estimation techniques. For instance, in one example, server 112 may comprise a computing system, such as computing system 300 depicted in FIG. 3, specifically configured to perform various steps, functions, and/or operations in connection with examples of the present disclosure for providing an access restriction of a second person to a location associated with a first person in a managed environment in connection with a physiological state of the second person. In this regard, server 112 may represent any one or more components of a cellular core network, a converged network, or the like, such as a presence server, a mobility management entity (MME), a home location register (HLR), and so forth. It should also be noted that the individual 140 may have consented to the collection and limited sharing of such information in accordance with the security plan in consideration of the person 130 allowing the possibility of individual 140 to gain access to the person 130. In other words, the monitoring of the various data associated with individual 140 is permitted with the full consent of individual 140 and/or with the authority given by a court order.

In one example, the entry gate 159 may be maintained in a closed position until it is confirmed that the individual 140 is to be allowed to pass. In one example, the entry gate 159 may be electromechanically closed. Alternatively, or in addition, an automated lock may be engaged to keep the entry gate 159 closed. In one example, the capturing of an image or voice of individual 140 may involve the individual 140 presenting himself or herself in front of camera 152 in order for a facial image to be captured, or speaking particular words into microphone 153. For instance, individual 140 may be made aware that in order to gain access via the entry gate 159, he or she may need to specifically approach the camera 152 or microphone 153 and comply with any instructions. For example, audio instructions may be provided to individual 140 via speaker 155 to stand in a particular place and face the camera 152, to repeat particular words into microphone 153, and so forth. In one example, individual 140 may be similarly instructed to place a finger on the fingerprint scanner 156.

In one example, processing unit 151 may store identification data relating to the individual 140 and may confirm or deny a match. However, in another example, biometric data regarding the approaching individual 140 may be captured via camera 152, microphone 153, and/or fingerprint scanner 156 and sent to security server 120 via processing unit 151. Similarly, any identification information regarding mobile device 141 may be captured via the wireless transceiver 154 and sent to security server 120 via processing unit 151. In turn, security server 120 may then compare any or all of the captured information to stored identification data regarding the individual 140 from the security plan.

In one example, when the security server 120 determines that there is a security plan pertaining to the individual 140, the security server 120 may also reference the time of day, and where within the managed environment 101 the individual 140 is located. For instance, if the time of day is a time for which the individual 140 is categorically excluded (e.g., during overnight hours) the individual 140 may be denied access via entry gate 159. However, if it is daytime or evening hours, then the security server 120 and/or security unit 150 may take further steps to determine the physiological state of the second person. For instance, camera 152 may capture a series of facial images which may then be compared by processing unit 151 and/or security server 120 to stored signatures, or classifiers for various physiological states. When the physiological state indicated from the facial images of individual 140 match an excluded physiological state from the security plan, individual 140 may be denied access via entry gate 159. Similarly, processing unit 151 and/or security server 120 may store or have access to video and/or audio signatures for various physiological states. If a video recording via camera 152 and/or an audio recording via microphone 153 matches an excluded physiological state (e.g., angry state, drunken state, emotionally disturbed state, etc.) from the security plan, individual 140 is to be denied access via entry gate 159.

In one example, a physiological state (e.g., an emotional state) of individual 140 may also be determined based upon the digital communications of individual 140, such as social media posts, emails, text messages, and so forth. For example, server 112 in telecommunication service provider network 110 may be permitted access of the digital communications of individual 140 in order to automatically compare words and phrases in outgoing communications of individual 140 to signatures, or classifiers for various emotional states. For instance, when words such as "hate," "mad," "angry," "rage," etc. may appear in the outgoing communications of individual 140, this may match a signature of one or more negative emotional states that would indicate individual 140 should be excluded from access to the person 130 according to the security plan. In one example, security server 120 may subscribe to access emotional state information regarding individual 140 from server 112 in the telecommunication server provider network 110. For example, individual 140 and/or person 130 may be subscribers of telecommunication service provider network 110 and may receive telecommunication services via mobile devices 131 and 141. Again, it should be noted that the individual 140 may have consented to the collection and limited sharing of such information in accordance with the security plan in consideration of person 130 allowing the possibility of individual 140 to access the person 130.

If the time of day, location, and/or physiological state(s) of individual 140 satisfy the parameters of the security plan, then the security server may open the entry gate 159, e.g., by sending an instruction to processing unit 151, or may cause the entry gate 159 to remain in an open position (if presently open), thereby allowing the individual 140 to access at least a portion of the managed environment 101. On the other hand, if access is to be denied, the security server may close the entry gate 159, e.g., by sending an instruction to processing unit 151, or may cause the entry gate 159 to remain in an closed position (if presently closed), thereby denying the individual 140 access to the managed environment 101. Security server 120 may also cause an audible warning to be presented to individual 140 via speaker 155, may capture a series of photographs or continue recording video via camera 152, record audio via microphone 153, and so on.

If, for example, it is during evening hours, the individual 140 may nevertheless be restricted to only open areas of the managed environment 101. For instance, security server 120 may detect, via security unit 160, that individual 140 is approaching the door 169. The detection of individual 140 may be the same or similar as described above in connection with detecting the individual 140 at or approaching entry gate 159 via security unit 150. However, in this case, since it is evening hours, the security server 120 may deny access by individual 140 to the building 135, which may comprise a "closed area" or "non-public area" according to the security plan.

It should be noted that a security plan may have any number of criteria/parameters for whether to allow or deny access by an individual. Thus, for example, a security plan for the person 130 pertaining to the individual 140 may also define that individual 140 is never allowed access to the vehicle 199 belonging to the person 130. For example, vehicle 199 may include security unit 190 which may communicate with security server 120 via wireless transceiver 194. As such, if security server 120 detects individual 140 approaching vehicle 199 via security unit 190, the security server 120 may cause the doors of vehicle 199 to be locked. Security server 120 may also cause an audible warning to be presented to individual 140 via speaker 195, may capture a series of photographs or continue recording video via camera 192, and so on.

In another example, a security plan may define that individual 140 may access a lobby area of building 135 (e.g., the first floor) when the individual is not in a restricted physiological state, but is not permitted beyond the lobby area. Thus, an access restriction may be applied by security server 120 at elevator 179 via security unit 170. In other words, security server 120 may send an instruction to the processing unit 171 of security unit 170 to close the doors of elevator 179, to cause the doors of elevator 179 to remain closed, to not allow the elevator 179 to move from the first floor, etc. Access doors to a stairwell of the building may also be closed/opened or locked/unlocked accordingly. As such, individual 140 must remain on the first floor of building 135 and await person 130, who is on the third floor in room 132, to come downstairs for the meeting.

In still another example, the security plan may not specify restrictions of individual 140 to any particular area, but may maintain a minimum separation distance between individual 140 and person 130. In such an example, the security server 120 may also determine the location of person 130 in the same or a similar manner as described above in connection with determining the location of individual 140. For instance, person 130 may be detected using facial recognition via a camera 152, 162, 172, 182, 192, etc., using voice recognition via a microphone 153, 163, 173, 183, 193, etc., by tracking a location of mobile device 131, and so forth. As such, the security server 120 may calculate a distance between person 130 and individual 140 to determine if one or more automated barriers in the managed environment 101 should be controlled to prevent a minimum separation between person 130 and individual 140 from being breached. As with previous examples, a notification or warning (e.g., of violation of a security plan and/or a legal restraining order underlying the security plan) may be presented to individual 140, e.g., via speakers 155, 165, 175, 185, and/or 195, via a message to the mobile device 141, and so forth. Alternatively, or in addition, a warning may be presented to person 130, e.g., speakers 155, 165, 175, 185, and/or 195, via a message to the mobile device 131, and so forth. Furthermore, the warning may include instructions to assist person 130 to avoid approaching individual 140, e.g., providing instructions to person 130 to travel in a direction that will create a greater separation between person 130 and individual 140.

In one example, when it is determined that individual 140 is present at or within managed environment 101 and access to person 130 is to be restricted in some way according to the security plan, a drone 105 may also be deployed to the location of individual 140, e.g., in addition to controlling one or more automated barriers, as an alternative or in addition to audio warning via speakers 155, 165, 175, 185, and/or 195, etc. For example, the security server 120 may be capable of recording the movements and actions of individual 140 via cameras 152, 162, 172, 182, and 192. However, there may be gaps in coverage such that there may be areas within managed environment 101 for which the cameras 152, 162, 172, 182, and 192 cannot capture video. A deployment of drone 105 by security server 120 may allow the security server to capture video and/or audio of individual 140 via a camera and/or a microphone (not shown) of the drone 105. In addition, a speaker of drone 105 (also not shown), may be used to present instructions or warnings to individual 140, thus providing a further deterrent to any malicious intentions. In one example, the drone 105 is guided to the individual 140 using location information gathered from device 141 of individual 140, e.g., GPS coordinates and the like.

Security server 120 may maintain control of drone 105 via wireless transceiver 122 and may provide, for example, GPS location information of mobile device 141 to the drone 105 with an instruction to hover over the location of mobile device 141 at a certain altitude while training a camera and/or light below. In another example, the drone 105 may be dispatched to an initial location where the individual 140 is detected. Drone 105 may then stream a video feed or series of photographs of the location to security server 120 from which the identity of individual 140 may be confirmed via facial recognition, gait recognition, etc. Upon detection, security server 120 may continue to maintain visual contact with individual 104 via drone 105 by sending updated instructions to reposition the drone 105, to re-train the camera and/or light of the drone 105, and so forth.

In one example, video and audio recording via cameras 152, 162, 172, 182, and 192, microphones 153, 163, 173, 183, and 193, and/or drone 105 may also be streamed by security server 120 to mobile device 131 of person 130 and/or to a device of security personnel or law enforcement. In one example, such video and/or audio recordings may also be stored for later presentation to person 130, security personnel, law enforcement, etc.

It should be noted that the system 100 has been simplified. In other words, the system 100 may be implemented in a different form than that illustrated in FIG. 1. For example, the system 100 may be expanded to include additional networks, and additional network elements (not shown) such as wireless transceivers and/or base stations, border elements, routers, switches, policy servers, security devices, gateways, a network operations center (NOC), a content distribution network (CDN) and the like, without altering the scope of the present disclosure. In addition, system 100 may be altered to omit various elements, substitute elements for devices that perform the same or similar functions and/or combine elements that are illustrated as separate devices.

As just one example, the operations described above with respect to security server 120 may alternatively or additionally be performed by server 112 in the telecommunication service provider network 110. For instance, components of managed environment 101 may be in communication with server 112 via wireless/cellular connections via wireless access network 115, or via a wired connection 125 via security server 120. In such case, security server 120 may serve as a data collection point/aggregator for data collected from security units 150, 160, 170, 180, and 190 and a distributor of instructions from server 112 for the respective security units 150, 160, 170, 180, and 190, and/or drone 105. In addition, although a single server 112 is illustrated in the example of FIG. 1, in other, further, and different examples the same or similar functions may be distributed among multiple devices within the telecommunication service provider network 110 that may collectively provide various services in connection with examples of the present disclosure for providing an access restriction of a second person to a location associated with a first person in a managed environment in connection with a physiological state of the second person.

In another example, a security plan may define that individual 140 should be denied access to person 130 when individual 140 is with a group of people. For instance, if security server 120 detects the presence of individual 140, e.g., via any one or more of the security units 150, 160, 170, 180, and 190 along with a group of people, the security server may deny access by controlling any of entry gate 159, door 169, elevator 179, door 189, and vehicle 199. The present of multiple people may be detected, for example, by capturing image or video and applying an image/pattern detection algorithm in order to determine that multiple individuals are present. In one example, a similar process may be used to detect multiple unique voices within an audio recording. In another example, a security plan may restrict access to person 130 by any individual (e.g., not specific to individual 140) exhibiting a certain type of behavior, physiological and/or emotional state. In addition, other types of automated barriers may be managed by security server 120 and/or server 112, such as windows of building 135, windows of vehicle 199, and so forth. In still another example, security server 120 and/or server 112 may control multiple automated barriers that may be determined to be situated between a location of the individual 140 and the location associated with person 130. For instance, upon detection of individual 140 in a physiological state that is subject to access restriction at gate 159, the gate 159 may be closed/locked. The security server 120 and/or server 112 may also cause doors 169 and 189 to be closed and/or locked (e.g., when the location associated with person 130 is the room 132), or only the access door of a stairwell to the third floor will be locked and the elevator will not stop on the third floor while access to other floors can still be allowed to minimize disruptions to other people residing in the managed environment 101. Thus, these and other modifications are all contemplated within the scope of the present disclosure.

Figure 2:
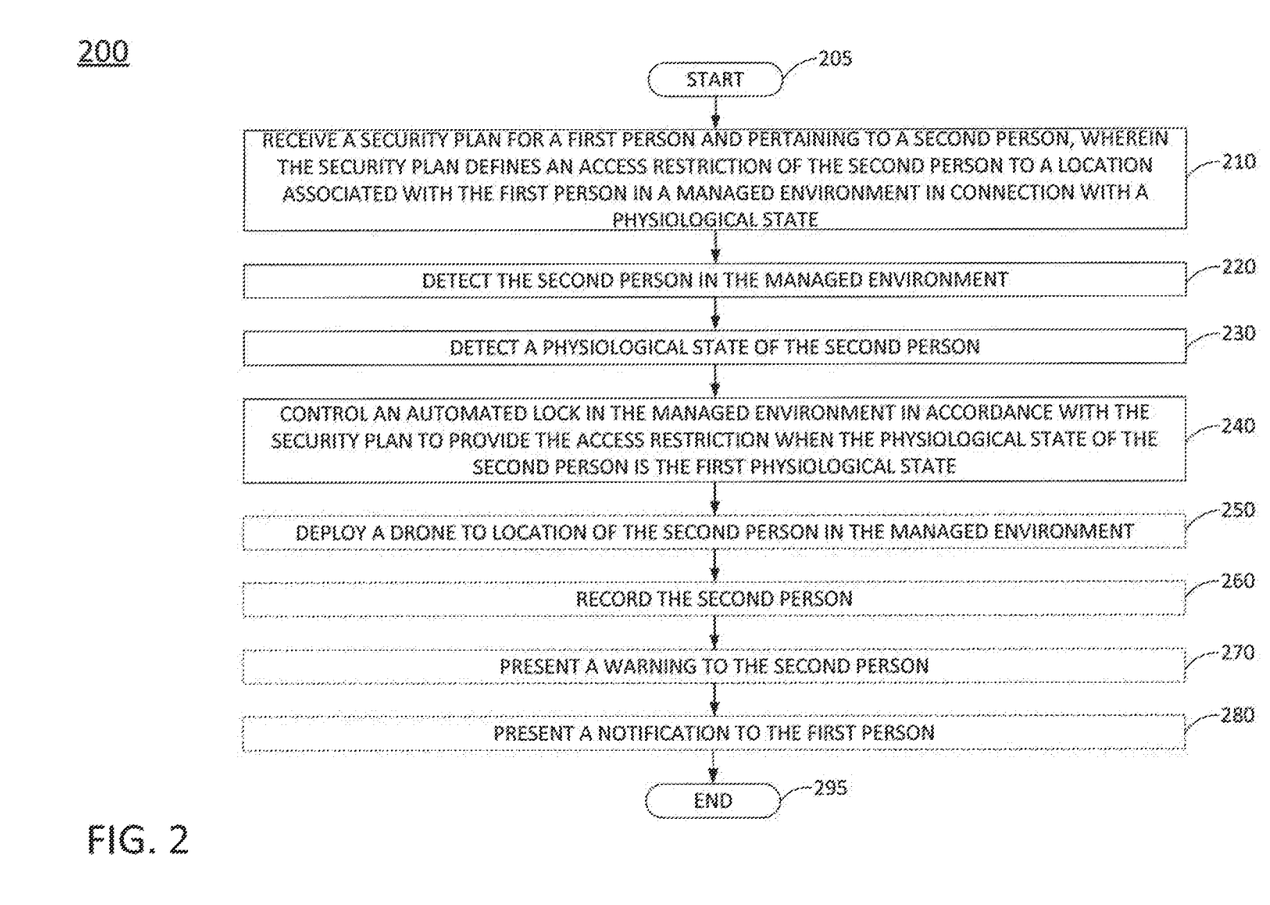
FIG. 2 illustrates a flowchart of an example method for providing an access restriction of a second person to a location associated with a first person in a managed environment in connection with a physiological state of the second person, in accordance with the present disclosure.

FIG. 2 illustrates a flowchart of an example method 200 for providing an access restriction of a second person to a location associated with a first person in a managed environment in connection with a physiological state of the second person. In one example, steps, functions and/or operations of the method 200 may be performed by a network-based device, such as security server 120 or server 112 in FIG. 1, or by security server 120 and server 112 in conjunction with one another and/or with other components of the system 100. In one example, the steps, functions, or operations of method 200 may be performed by a computing device or processing system 300, and/or processor 302 as described in connection with FIG. 3 below. Similarly, in one example, the steps, functions, or operations of method 200 may be performed by a processing system comprising one or more computing devices collectively configured to perform various steps, functions, and/or operations of the method 200. For instance, multiple instances of the computing device or processing system 300 may collectively function as a processing system, e.g., comprising a security server, and/or a security server in conjunction with other components. For illustrative purposes, the method 200 is described in greater detail below in connection with an example performed by a processor, such as processor 302. The method begins in step 205 and proceeds to step 210.

At step 210, the processor receives a security plan for a first person that pertains to a second person. In one example, the security plan defines an access restriction of the second person to a location associated with the first person in a managed environment in connection with a physiological state, or multiple physiological states, of the second person. In one example, the second person has consented to the security plan. For example, the second person may have agreed to allow location information to be obtained from the mobile device of the second person and/or a cellular network provider. In one example, the second person may have further agreed to saliva and/or fingerprint analysis, facial recognition, voice analysis, and so forth. In this regard, the second person may have consented to storage of various types of identification information including, biometric information such as photographs, voice recordings, video recordings, fingerprints, and the like, as well as telephone numbers, MAC addresses, license plate numbers, and so on that are associated with the second person. However, in other examples any one or more of these types of information regarding the second person may be unilaterally provided by the first person or a court order. In one example, the managed environment may be a building, a residential development, an office complex, a campus, and so forth. For instance, the managed environment may include a single family home or multi-dwelling type development, an apartment building, an office building, a condominium and/or apartment complex, a gated community, a hospital campus, a school, a college or university campus, a corporate campus, and so forth.

In one example, the location associated with the first person in the managed environment is detected via at least one of: a wireless communication between a wireless transceiver in the managed environment and a device of the first person, location information of the mobile device of the first person obtained via a cellular network provider, or a biometric detection of the first person in the managed environment. The biometric detection of the first person in the managed environment may include a facial recognition via a camera deployed the managed environment, a voice detection via a microphone deployed in the managed environment, a gait detection via the camera deployed in the managed environment, a fingerprint scan of the first person in the managed environment, a detection of an identification badge, key fob, or the like associated with the first person, and so on. The location associated with the first person may comprise, for example, a current location of the first person, a current location of a mobile device of the first person, a residence of the first person, a classroom of the first person, a work location of the first person, or a vehicle of the first person. Thus, the location associated with the first person can be a location where the first person is, a location frequented by the first person, or a location where an object of the first person is currently located.

At step 220, the processor detects the second person in the managed environment. The second person may be detected in the managed environment via at least one of: a wireless communication between a wireless transceiver in the managed environment and a mobile device of the second person, location information of the mobile device of the second person obtained via a cellular network provider, or a biometric detection of the second person in the managed environment. The biometric detection of the second person in the managed environment may comprise a facial recognition via a camera deployed the managed environment, a voice detection via a microphone deployed in the managed environment, or a gait detection via the camera deployed in the managed environment, or a combination of any of such factors. In one example, the biometric detection is based upon a biometric reference for the second person that is contained in the security plan, e.g., a stored photograph or Eigen-face, a stored video or audio sample, a stored fingerprint, and so forth.

At step 230, the processor detects at least one physiological state of the second person. In one example, the physiological state (or states) of the second person is determined via a camera in the managed environment and/or a microphone in the managed environment. For instance, captured audio or video recordings may be compared to stored signatures for various physiological (e.g., biometric and/or emotional) states. For instance, the processor may apply one or more discriminative classifiers (e.g., a support vector machine (SVM)-based classifier, such as a binary classifier or a multi-class SVM-based classifier, a decision tree algorithm, or the like) to the captured audio or video recordings in order to detect one or more physiological states. Alternatively, or in addition, the physiological state(s) of the second person may be determined from the second person's digital communications, such as social media posts, emails, text messages, and so forth. In such an example, the physiological states may be determined via application of one or more classifiers representing the physiological states, based upon keyword matching, and so forth.

In one example, the physiological state(s) of the second person may be determined from a fingerprint scan, e.g., to detect the presence of a controlled substance in the second person. In one example, the physiological state(s) may comprise at least one of: an under the influence of a controlled substance state, an off-medication state, an in possession of a dangerous item state, or a negative emotional state. For instance, the under the influence of a controlled substance state is determined via at least one of: a fingerprint scan, a pupil scan, a breath analyzer analysis, or a saliva analysis. In the case where a fingerprint scan is utilized, the fingerprint scan may be provided via a scanner deployed in the managed environment or via a mobile device of the second person. In the case where a pupil scan is utilized, the pupil scan may be provided via a scanner deployed in the managed environment or via a mobile device of the second person. In the case where a breath analyzer analysis is utilized, the breath analyzer analysis may be provided via a breath analyzer deployed in the managed environment or via a mobile device of the second person. In the saliva analysis example, the saliva analysis may be provided via a portable spectrometer of the second person.

In one example, step 230 may include determining a particular location of the second person within the managed environment and detecting that the second person is within a predefined proximity of the location associated with the first person in accordance with the security plan. For instance, some security plans may allow for the second person to generally be present in the managed environment and may only apply access restrictions if and when the second person is too close to the location associated with the first person. Thus, the location associated with the first person and the location of the second person may be compared to determine whether the separation distance remains compliant with the security plan. In addition, in one example, step 230 may be performed when other threshold parameters are satisfied. For example, the security plan may allow for the second person to access the first person during all daytime hours, and only provides for an access restriction in the evening and overnight hours. As such, if it is during daytime hours, there may be no need to determine the physiological state of the second person.

At step 240, the processor controls an automated or remotely controllable barrier in the managed environment in accordance with the security plan to provide the access restriction when the physiological state (e.g., a negative physiological state) of the second person is detected. The automated or remotely controllable barrier may comprise, for example, a door, an elevator, a gate, a window, or a barricade. In one the example, the controlling of the automated or remotely controllable barrier may comprise activating a lock, maintaining a door, barricade, elevator, or the like in a closed position, closing a gate or door, elevating a barricade, preventing an elevator from operating, deactivating a vehicle, and so forth. As such, the state of the automated or remotely controllable barrier is changed from a first state to a second state.

At optional step 250, the processor may deploy a drone to a location of the second person in the managed environment. For instance, as described above, the drone may be activated with instructions to hover over and/or track the location where the second person is detected in the managed environment. The location information may include GPS coordinates of a mobile device of the second person or a location of a security unit via which the second person is detected, for example.

At optional step 260, the processor may record the second person in the managed environment. For instance, the second person may be recorded via one or more microphones in the managed environment, via a drone deployed at optional step 250, and so forth. The recording may be stored for later presentation to the first person, security personnel of the managed environment, law enforcement, etc.

At optional step 270, the processor may present a warning to the second person. The warning may comprise an audio, text, video, or multimedia warning presented via one or more cameras and/or microphones in the managed environment, via a display screen in the managed environment, via a drone deployed at optional step 250, and so forth. In one example, a warning may be presented via a mobile device of the second person. For instance, a text message alert or an instruction to an application for automatically presenting audible warning messages may be sent to the mobile device of the second person with instructions to leave the current location or the managed environment entirely.

At optional step 280, the processor may present a notification to the first person via at least one of: a mobile device of the first person, a speaker in the managed environment, or a display screen in the managed environment. In one example, audio and/or video recording of the second person that may be recorded at optional step 260 may also be streamed to the mobile device of the first person.

Following step 240, or any of optional steps 250-280, the method 200 may proceed to step 295. At step 295, the method 200 ends.

It should be noted that the method 200 may be expanded to include additional steps. For instance, in one example the method 200 may further include automatically sending notifications to security personnel or law enforcement of a violation of a security plan by the second person following step 230. In another example, the processor may present, via the mobile device of the first person, an option to override an access restriction that may be automatically applied at step 240. In another example, the processor may present, via the mobile device of the first person, an instruction as to how to avoid the second person immediately, e.g., directions to travel that will increase the distance separating the first person and the second person. Thus, these and other modifications are all contemplated within the scope of the present disclosure.

In addition, it should be noted that although not specifically specified, one or more steps, functions or operations of the method 200 may include a storing, displaying and/or outputting step as required for a particular application. In other words, any data, records, fields, and/or intermediate results discussed in the respective methods can be stored, displayed and/or outputted to another device as required for a particular application. Furthermore, steps or blocks in FIG. 2 that recite a determining operation or involve a decision do not necessarily require that both branches of the determining operation be practiced. In other words, one of the branches of the determining operation can be deemed as an optional step. In addition, one or more steps, blocks, functions, or operations of the above described method 200 may comprise optional steps, or can be combined, separated, and/or performed in a different order from that described above, without departing from the example embodiments of the present disclosure.

FIG. 3 depicts a high-level block diagram of a computing device or processing system specifically programmed to perform the functions described herein. As depicted in FIG. 3, the processing system 300 comprises one or more hardware processor elements 302 (e.g., a central processing unit (CPU), a microprocessor, or a multi-core processor), a memory 304 (e.g., random access memory (RAM) and/or read only memory (ROM)), a module 305 for providing an access restriction of a second person to a location associated with a first person in a managed environment in connection with a physiological state of the second person, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 200 as discussed above is implemented in a distributed or parallel manner for a particular illustrative example, i.e., the steps of the above method 200, or the entire method 200 is implemented across multiple or parallel computing devices, e.g., a processing system, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method 200. In one embodiment, instructions and data for the present module or process 305 for providing an access restriction of a second person to a location associated with a first person in a managed environment in connection with a physiological state of the second person (e.g., a software program comprising computer-executable instructions) can be loaded into memory 304 and executed by hardware processor element 302 to implement the steps, functions or operations as discussed above in connection with the illustrative method 200. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 305 for providing an access restriction of a second person to a location associated with a first person in a managed environment in connection with a physiological state of the second person (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A method comprising:
   receiving, by a processing system including a processor, a security plan for a first person that pertains to a second person, wherein the security plan defines a physical access restriction of the second person to a location in a managed environment in connection with a physiological state of the second person and a time restriction, wherein the first person and the second person are different persons;
   detecting, by the processing system, the second person within a predefined proximity of the location in the managed environment and a current time;
   detecting, by the processing system, the physiological state of the second person, in accordance with the security plan; and
   controlling, by the processing system, a physical automated barrier in the managed environment in accordance with the security plan to provide the time restriction based on the current time and the physical access restriction when the physiological state of the second person is detected.

2. The method of claim 1, wherein the location comprises:
   a current location of the first person;
   a current location of a mobile device of the first person;
   a residence of the first person;
   a classroom of the first person;
   a work location of the first person; or
   a vehicle of the first person.

3. The method of claim 1, wherein the managed environment comprises:
   a building;
   a residential complex;
   an office complex; or
   a campus.

4. The method of claim 1, wherein the location in the managed environment is detected via at least one of:
   a wireless communication between a wireless transceiver in the managed environment and a mobile device of the first person;
   location information of the mobile device of the first person obtained via a cellular network provider; or
   a biometric detection of the first person in the managed environment.

5. The method of claim 4, wherein the biometric detection of the first person in the managed environment comprises at least one of:
   a facial recognition via a camera deployed in the managed environment;
   a voice detection via a microphone deployed in the managed environment; or
   a gait detection via the camera deployed in the managed environment.

6. The method of claim 1, wherein the second person is detected in the managed environment via at least one of:
   a wireless communication between a wireless transceiver in the managed environment and a mobile device of the second person;
   location information of the mobile device of the second person obtained via a cellular network provider; or
   a biometric detection of the second person in the managed environment.

7. The method of claim 6, wherein the biometric detection of the second person in the managed environment comprises at least one of:
   a facial recognition via a camera deployed in the managed environment;
   a voice detection via a microphone deployed in the managed environment; or
   a gait detection via the camera deployed in the managed environment.

8. The method of claim 6, wherein the biometric detection is based upon a biometric reference for the second person that is contained in the security plan.

9. The method of claim 1, wherein the physiological state of the second person is determined via at least one of:
   a camera input; or
   a microphone input.

10. The method of claim 1, wherein the physiological state comprises at least one of:
    an under an influence of a controlled substance state;
    an off-medication state;
    an in possession of a dangerous item state; or
    a negative emotional state.

11. The method of claim 10, wherein the under the influence of the controlled substance state is determined via at least one of:
    a fingerprint scan;
    a pupil scan;
    a breath analysis; or
    a saliva analysis.

12. The method of claim 11, wherein the fingerprint scan or the pupil scan is provided via:
    a scanner deployed in the managed environment; or
    a mobile device of the second person.

13. The method of claim 11, wherein the saliva analysis or the breath analysis is provided via a portable spectrometer or via a breath analyzer of the second person.

14. The method of claim 1, further comprising:
deploying a drone to a location of the second person in the managed environment.

15. The method of claim 14, further comprising at least one of:
recording the second person via the drone; or
presenting a warning to the second person via the drone.

16. The method of claim 1, further comprising:
presenting a warning to the second person via at least one of:
a device in the managed environment; or
a mobile device of the second person.

17. The method of claim 1, further comprising:
presenting a notification to the first person via at least one of:
a mobile device of the first person; or
a device in the managed environment.

18. The method of claim 1, wherein the physical automated barrier comprises:
a door;
an elevator;
a gate;
a window; or
a barricade.

19. A non-transitory computer-readable medium storing instructions which, when executed by a processing system including a processor, cause the processing system to perform operations, the operations comprising:
receiving a security plan for a first person that pertains to a second person, wherein the security plan defines a physical access restriction of the second person to a location in a managed environment in connection with a physiological state of the second person and a time restriction, wherein the first person and the second person are different persons;
detecting the second person within a predefined proximity of the location in the managed environment and a current time;
detecting the physiological state of the second person, in accordance with the security plan; and
controlling a physical automated barrier in the managed environment in accordance with the security plan to provide the time restriction based on the current time and the physical access restriction when the physiological state of the second person is detected.

20. A device comprising:
a processing system including a processor; and
a non-transitory computer-readable medium storing instructions which, when executed by the processing system, cause the processing system to perform operations, the operations comprising:
receiving a security plan for a first person that pertains to a second person, wherein the security plan defines a physical access restriction of the second person to a location in a managed environment in connection with a physiological state of the second person and a time restriction, wherein the first person and the second person are different persons;
detecting the second person within a predefined proximity of the location in the managed environment and a current time;
detecting the physiological state of the second person, in accordance with the security plan; and
controlling a physical automated barrier in the managed environment in accordance with the security plan to provide the time restriction based on the current time and the physical access restriction when the physiological state of the second person is detected.

* * * * *